US011255714B2

(12) United States Patent
Blodt et al.

(10) Patent No.: US 11,255,714 B2
(45) Date of Patent: Feb. 22, 2022

(54) APPARATUS FOR DETERMINING AND/OR MONITORING AT LEAST ONE PROCESS VARIABLE

(71) Applicant: Endress + Hauser GmbH + Co. KG, Maulburg (DE)

(72) Inventors: Thomas Blodt, Steinen (DE); Tobias Brengartner, Emmendingen (DE); Benjamin Mack, Lorrach (DE); Peter Klofer, Steinen (DE)

(73) Assignee: ENDRESS+HAUSER SE+CO.KG, Maulburg (DE)

( * ) Notice: Subject to any disclaimer, the term of this patent is extended or adjusted under 35 U.S.C. 154(b) by 0 days.

(21) Appl. No.: 15/747,192

(22) PCT Filed: Jul. 26, 2016

(86) PCT No.: PCT/EP2016/067712
§ 371 (c)(1),
(2) Date: Jan. 24, 2018

(87) PCT Pub. No.: WO2017/017076
PCT Pub. Date: Feb. 2, 2017

(65) Prior Publication Data
US 2018/0224318 A1 Aug. 9, 2018

(30) Foreign Application Priority Data

Jul. 30, 2015 (DE) .................. 10 2015 112 543.9

(51) Int. Cl.
*G01F 23/296* (2006.01)
*G01F 23/284* (2006.01)
(Continued)

(52) U.S. Cl.
CPC ........ *G01F 23/2966* (2013.01); *G01F 23/284* (2013.01); *G01N 9/002* (2013.01);
(Continued)

(58) Field of Classification Search
CPC .......................... G01F 25/2966; G01F 23/284
(Continued)

(56) References Cited

U.S. PATENT DOCUMENTS 2,435,487 A * 2/1948 Adler ................. H03B 5/30
331/157
3,523,446 A * 8/1970 Kratky ................. G01N 9/002
73/32 A
(Continued)

FOREIGN PATENT DOCUMENTS

CN 10 3080706 A 5/2013
CN 10 4142167 A 11/2014
(Continued)

*Primary Examiner* — John Fitzgerald
*Assistant Examiner* — Rodney T Frank
(74) *Attorney, Agent, or Firm* — Bacon & Thomas, PLLC (57) ABSTRACT

An Apparatus for determining and/or monitoring at least one process variable of a medium in a container, comprising: a mechanically oscillatable unit a driving/receiving unit for exciting the mechanically oscillatable unit to execute mechanical oscillations by means of an electrical, exciting signal and for receiving and transducing the mechanical oscillations into an electrical, received signal a control unit, which is embodied to produce the exciter signal starting from the received signal and to set a predeterminable phase shift between the exciter signal and the received signal, an electromagnetically oscillatable unit, an active element for producing and/or maintaining electromagnetic oscillations in the electromagnetically oscillatable unit, which active element forms together with the electromagnetically oscillatable unit an oscillator, a coupling unit, which is embodied to tap an output signal from the active element, and an evaluation unit, which evaluation unit is embodied to determine the at least one process variable from the received signal and/or from the output signal.

15 Claims, 4 Drawing Sheets

(51) Int. Cl.
- *G01N 9/00* (2006.01)
- *G01N 11/16* (2006.01)
- *G01N 27/02* (2006.01)
- *G01N 33/03* (2006.01)
- *G01N 33/28* (2006.01)

(52) U.S. Cl.
CPC ............ *G01N 11/16* (2013.01); *G01N 27/02* (2013.01); *G01N 33/03* (2013.01); *G01N 33/2847* (2013.01); *G01N 2009/006* (2013.01)

(58) Field of Classification Search
USPC .......................................................... 73/32 A
See application file for complete search history.

(56) References Cited

U.S. PATENT DOCUMENTS

| | | | | |
|---|---|---|---|---|
| 3,756,074 A | * | 9/1973 | Hedvig | G01N 3/38 374/48 |
| 4,096,745 A | * | 6/1978 | Rivkin | G01F 1/74 73/32 A |
| 2006/0031030 A1 | | 2/2006 | Bennett et al. | |
| 2010/0049455 A1 | * | 2/2010 | Scholtz | H02P 9/105 702/60 |
| 2011/0016990 A1 | * | 1/2011 | Huber | G01F 1/8427 73/861.357 |
| 2011/0023624 A1 | * | 2/2011 | Huber | G01F 1/8409 73/861.357 |
| 2011/0080227 A1 | * | 4/2011 | Aoyama | B06B 1/0238 331/186 |
| 2013/0338943 A1 | * | 12/2013 | Kolahi | G01F 1/8436 702/46 |

FOREIGN PATENT DOCUMENTS

| | | |
|---|---|---|
| DE | 1766977 A1 | 9/1971 |
| DE | 100 57 974 A1 | 5/2002 |
| DE | 203 20 382 U1 | 7/2004 |
| DE | 10 2004 059 050 A1 | 6/2006 |
| DE | 10 2005 050 400 A1 | 4/2007 |
| DE | 203 21 736 U1 | 6/2009 |
| DE | 10 2010 038 535 A1 | 2/2012 |
| DE | 10 2012 020 925 A1 | 4/2014 |
| DE | 10 2013 112 025 A1 | 4/2015 |
| DE | 10 2015 112 543 A1 | 2/2017 |
| WO | 2004/017025 A1 | 2/2004 |
| WO | 2008/006391 A1 | 1/2008 |

\* cited by examiner

APPARATUS FOR DETERMINING AND/OR MONITORING AT LEAST ONE PROCESS VARIABLE

TECHNICAL FIELD

The invention relates to an apparatus for determining and/or monitoring at least one process variable of a medium.

BACKGROUND DISCUSSION

Corresponding field devices of process- and/or automation technology are based, depending on process variable to be determined, on many different principles, which are known per se from the state of the art. In such case, a particular field device can either be capable of registering an individual process variable, or, especially simultaneously, a number of process variables. For a comprehensive characterizing of the properties, especially physical and/or chemical properties, of a medium, however, as a rule, a number of field devices must be applied in parallel.

A field device typically includes at least one sensor element coming, directly or indirectly, at least partially and at least at times, in contact with the process, as well as an electronics unit, which serves, for example, for signal registration,—evaluation and/or—feeding. For example, the sensor element of a vibronic fill-level measuring device includes typically at least one mechanically oscillatable unit, such as, for example, an oscillatory fork, a single rod or a membrane. This is excited during operation by means of a driving/receiving unit, frequently in the form of an electromechanical transducer unit, to execute mechanical oscillations. The electromechanical transducer unit can be, for example, a piezoelectric drive or an electromagnetic drive. It is noted here that the driving/receiving unit can be, depending on embodiment of the measuring device, either a separate drive unit and a separate receiving unit, or a combined driving/receiving unit.

Vibronic fill level measuring devices are produced by Endress+Hauser in a great variety of forms and are sold, for example, under the marks, LIQUIPHANT and SOLIPHANT. The underpinning measuring principles are generally known from a large number of publications. The driving/receiving unit excites the mechanically oscillatable unit by means of an electrical, exciting signal to execute mechanical oscillations. Conversely, the driving/receiving unit can receive the mechanical oscillations of the mechanically oscillatable unit and transduce them into an electrical, received signal. The driving/receiving unit is in many cases part of a fed back, electrical, oscillatory circuit, by means of which the exciting of the mechanically oscillatable unit to execute mechanical oscillations occurs. For example, for a resonant oscillation, the oscillatory circuit condition must be fulfilled, according to which the sum of all amplifications in the oscillatory circuit, or the amplification factor, is 1 and all phases arising in the oscillatory circuit sum to a multiple of 360°.

For exciting and fulfilling the oscillatory circuit condition, a certain phase shift between the exciting signal and the received signal must be assured. Therefore, frequently, a predeterminable value is set for the phase shift, thus a desired value for the phase shift between the exciting signal and the received signal. Known for this from the state of the art are the most varied of solutions, both analog as well as also digital. In principle, the adjusting of the phase shift can be performed, for example, by applying a suitable filter, or also by means of a control loop controlled to a predeterminable phase shift, the desired value. Known from German patent, DE102006034105A1, for example, is a tunable phase shifter. The additional integration of an amplifier with adjustable amplification factor for additional control of the oscillation amplitude is, in contrast, described in German patents, DE102007013557A1 and DE102005015547A1 provides the application of an allpass filter. The setting of the phase shift is, moreover, possible by means of a frequency sweep procedure, such as disclosed, for example, in German patents, DE102009026685A1, DE102009028022A1 and DE102010030982A1. The phase shift can, however, also be controlled by means of a phase locked loop (PLL) to a predeterminable value. Such an excitation method is subject matter of German patent, DE102010030982A1.

Both the exciting signal as well as also the received signal are characterized by frequency f, amplitude A and/or phase $\phi$. Correspondingly, changes in these variables are usually taken into consideration for determining the process variable, such as a predetermined fill level, a flow, the density and/or the viscosity. In the case of a vibronic limit level switch for liquids, for example, it is distinguished whether the oscillatable unit is covered by the liquid or freely oscillating. These two states, the free state and the covered state, are distinguished, in such case, for example, based on different resonance frequencies, thus a frequency shift, in the case of presence of a predeterminable phase shift between exciting signal and received signal. The density and/or viscosity can, in turn, be ascertained with such a measuring device only when the oscillatable unit is covered by the medium.

Known from German patent, DE10057974A1 for determining and/or monitoring the density of a medium are a method and an apparatus, by means of which the influence of at least one disturbing variable, for example, viscosity, on the oscillation frequency of the mechanically oscillatable unit is ascertained and correspondingly compensated. Described in German patent, DE102006033819A1, furthermore, is the setting of a predeterminable phase shift between the exciting signal and the received signal, a phase shift where effects of changes of the viscosity of the medium on the mechanical oscillations of the mechanically oscillatable unit are negligible. In such case, the density is determined essentially according to the formula $$\rho_{Med} = \frac{1}{K}\left[\left(\frac{f_{0,Vak} + C \cdot t + A \cdot t^2}{f_{T,P,Med}}\right)^2 \cdot (1 + D \cdot p) - 1\right]$$

wherein K is the density sensitivity of the mechanically oscillatable unit, $f_{0,Vak}$ the frequency of the mechanical oscillations in vacuum, C and A, respectively, the linear and quadratic temperature coefficients of the mechanically oscillatable unit, t the process temperature, $f_{T,P,Med}$ the frequency of the mechanical oscillations in the medium, D the pressure coefficient, and p the pressure of the medium.

The viscosity of a medium can be determined by means of a vibronic sensor based on the phase versus frequency curve ($\phi=g(f)$), such as described, for example, in German patent, DE10050299A1. This procedure is based on the dependence of the damping of the oscillatable unit on the viscosity of the medium. In such case, the lower the viscosity is, the steeper is the phase versus frequency curve. In order to eliminate the influence of density on the measuring, the viscosity is determined based on a frequency change caused by two different values for the phase, thus by means of a relative measurement. In this regard, either two different phase values can be set and the associated frequency change determined, or a predetermined frequency band is moved through and it is detected when at least two predetermined phase values are achieved.

Known from German patent, DE102007043811A1, moreover, is to ascertain from a change of the eigenfrequency and/or resonant frequency and/or the phase relationship a change of the viscosity and/or to determine the viscosity based on correspondingly furnished dependencies of the oscillations of the oscillatable unit on the viscosity of the medium. Also in the case of this procedure, the dependence of the viscosity on the density of the medium must be taken into consideration.

Summarizing, use of a vibronic fill-level measuring device enables both the determining and/or monitoring of a predeterminable fill level, especially a limit level, as well as also the determining of the density and/or viscosity of the medium, in case the oscillatable unit is covered by medium. Other process variables required for characterizing a medium are only ascertainable by applying at least one additional measuring device based on another principle.

SUMMARY OF THE INVENTION

An object of the present invention, therefore, is to provide an apparatus for determining and/or monitoring at least one process variable and having an expanded domain of application.

This object is achieved by an apparatus for determining and/or monitoring at least one process variable of a medium in a container, comprising
- a mechanically oscillatable unit,
- a driving/receiving unit for exciting the mechanically oscillatable unit to execute mechanical oscillations by means of an electrical, exciting signal and for receiving and transducing the mechanical oscillations into an electrical, received signal,
- a control unit, which is embodied to produce the exciter signal starting from the received signal and to set a predeterminable phase shift between the exciter signal and the received signal,
- an electromagnetically oscillatable unit,
- an active element for producing and/or maintaining electromagnetic oscillations in the electromagnetically oscillatable unit, which active element forms together with the electromagnetically oscillatable unit an oscillator,
- a coupling unit, which is embodied to tap an output signal from the active element, and
- an evaluation unit, which evaluation unit is embodied to determine the at least one process variable from the received signal and/or from the output signal.

According to the invention, the mechanically oscillatable unit is at least part of a first sensor element and the electromagnetically oscillatable unit at least part of a second sensor element. In the case of the apparatus of the invention, of concern is a combination of a vibronic fill-level measuring device and a measuring device in the form of a so-called microwave resonator, microwave oscillatory system or microwave oscillator. Such is also referred to in the following as a microwave sensor. Advantageously in this way, a clearly expanded domain of application can be achieved in comparison with a conventional vibronic fill-level measuring device. This relates both to the accessibility of an enlarged number of determinable process variables as well as variables derivable therefrom by means of mathematical relationships, as well as also to the opportunity of being able to execute expanded diagnostic functions concerning the state of at least one of the two sensor elements.

Measuring devices in the form of microwave sensors are known per se from the state of the art and are described, for example, in the Offenlegungsschriften (laid open German applications) DE102012104075A1, DE102013112025A1 and DE102013112026A1. The disclosure of these Offenlegungsschriften is to be correspondingly associated comprehensively with that of the present invention. In the case of a corresponding measuring device, the particular process variable is ascertainable based on an electromagnetic field, which is influenced by the presence, at least partially and/or at times, of a medium.

In this regard, a so-called frequency determining element, which is, in this case, the electromagnetically oscillatable unit of an oscillator, especially a high-frequency oscillator with frequencies in the range from 10 MHz to, for instance, 10 GHz, is arranged in such a manner that it is located, at least at times and/or partially, in the immediate vicinity of the medium, or measured medium. As a function of the particular medium, then the oscillation characteristics of the oscillator change, based on which determination of the desired process variable can occur.

At least for producing and maintaining the electromagnetic oscillations, the oscillator includes a so-called active element, which is, for example, an amplifier. The active element is especially designed in such a manner that, on the one hand, an electromagnetic oscillation within the oscillator can be maintained and, on the other hand, an output signal corresponding to the oscillations in the oscillator can be coupled out via a so-called out-coupling element, in the present case part of the coupling unit, without influencing the oscillatory behavior of the oscillator. Based on the output signal, finally, the particular process variable is ascertained. The high-frequency oscillator can be, among other things, a feed back oscillator or also a reflex oscillator. The construction of a suitable high-frequency oscillator can be learned, for example, from (laid open German application) Offenlegungsschrift DE102011078060A1.

In the following, by way of example, some preferred embodiments of a measuring device of the invention will now be described along with resulting advantages. These explanations do not represent an exclusive list of possible applications and embodiments.

In different embodiments, the mechanically oscillatable unit is a membrane, a single rod, or an oscillatory fork. The mechanically oscillatable unit can be manufactured advantageously of a metal, a ceramic or a synthetic material, e.g. a plastic. Depending on positioning of the electromagnetically oscillatable unit, especially the application of a synthetic material for the mechanically oscillatable unit can prove to be especially advantageous. If the electromagnetically oscillatable unit is, for example, at least partially positioned at least within a portion of the mechanically oscillatable unit, then a synthetic material offers, on the one hand, a high transmittance of microwave radiation. On the other hand, the synthetic material at least partially surrounding the electromagnetically oscillatable unit represents an effective barrier against the particular medium, and, thus, for example, a protection of the electromagnetically oscillatable unit from corrosion.

In an embodiment, the driving/receiving unit includes at least one piezoelectric element or at least one coil. The most varied of embodiments are known for piezoelectric driving/receiving units of vibronic sensors. A corresponding electromechanical transducer unit with at least one piezoelectric element includes at least one transmitting unit or transmission electrode and a receiving unit or receiving electrode. In some cases, moreover, also at least one reference electrode is provided, for example, serving as a ground potential, but even a floating reference electrode is possible. Examples of embodiments in the case of a so-called bimorph-drive are disclosed, for instance, in European patent, EP0751380B1. So called stack-drives are, in contrast, for example, described in European patents, EP0875741B1, EP1134038A1, EP1277243B1 and EP19969005B1 and a so called four-quadrants drive is subject matter, for instance, of European patent, EP128105161.

In contrast, in the case of a so-called electromagnetic driving/receiving unit, the changing of electrical energy into mechanical energy occurs via a magnetic, alternating field, by means of which a periodic force is transmitted to the mechanically oscillatable unit. Also for this principle of an electromechanical transducer unit, which, as a rule, includes at least one coil and one magnet, numerous embodiments are known, such as, for example, those described in the documents published international applications, WO 2007/113011 and WO 2007/114950 A1.

In an additional embodiment, the electromagnetically oscillatable unit is embodied as a waveguide, especially as a coaxial cable, hollow conductor, or microstrip transmission line, as a patch antenna, as a gradient conductor, especially a dielectric gradient conductor or as a two-wire line. Fundamentally, the electromagnetically oscillatable unit is formed in such a manner that electromagnetic waves can propagate in it. In the case of embodiment as a waveguide, the electromagnetically oscillatable unit can be present, for example, in a cable form, such as in the case of a ribbon conductor with two Litz wires, wires or other conductors with fixed separation, or a line with a shared shield, such as, for example, in the case of a coaxial cable. Furthermore, known are so-called tube shapes, such as e.g. in the case of hollow conductors, which, among others, can be present in which form of metal tubes with rectangular or circularly shaped cross section, or also strip conductors, such as, for example, a microstrip transmission line. Referred to as a patch antenna is, as a rule, an antenna form, in the case of which a frequently rectangular metal surface acts as a resonator. Furthermore, a two-wire line can be, for example, a so-called ribbon conductor. A gradient conductor is, finally, for example, a light waveguide, especially a multimode, glass fiber. Preferably, it is a multimode, glass fiber with a predeterminable gradient index profile. Used for such a multimode, glass fiber are so-called gradient index fibers, or also gradient fibers, in the case of which the index of refraction falls outwardly continuously from the fiber core. A gradient conductor can advantageously be constructed completely of a synthetic material.

In a preferred embodiment, the at least one process variable is a fill level or limit-level of the medium in the container, the viscosity, the density, the permittivity, the permeability, the dielectric loss factor, the protein content and/or fat content of a medium, especially a food, or the water content of an oil. This list of the ascertainable process variables is, in such case, not exclusive. With the apparatus of the invention, a predeterminable fill level can be ascertained using both oscillatable units. Moreover, the electromagnetically oscillatable unit offers in the case of comparatively small containers also the opportunity of registering a continuous fill level. The density and/or viscosity of the medium can be determined based on an evaluation of the mechanical oscillations of the mechanically oscillatable unit. In contrast, the permittivity, also referred to as dielectric conductivity, or the permeability, or also magnetic conductivity, which are measures of the permeability of a certain medium for electrical and magnetic fields, can be ascertained by means of the electromagnetically oscillatable unit, for example, by means of the complex index of refraction, which is likewise determinable. The dielectric loss factor likewise ascertainable using the electromagnetically oscillatable unit is, in turn, a measure for the dissipation of electromagnetic energy within the oscillator, and therewith a measure for the degree of damping, or attenuation, of the propagating electromagnetic waves.

The protein content and/or fat content of a medium can, in turn, be determined from a combination of the process variables, the primittivity, the dielectric loss factor, the transmittance and degree of reflection as well as the density and/or viscosity. In such case, there results in the case of the electromagnetically oscillatable unit for a fat a comparatively low permittivity at comparatively low dielectric loss factor, while in the case of a protein there is a comparatively low permittivity coupled with a comparatively high dielectric loss factor. The determining of the water fraction in an oil is described at length in German patent, DE102013112025A1. Regarding the salt content of a medium, (cooking) salt has a permittivity, or a dielectric constant, of 5.9 independently of temperature. Furthermore, there occurs in reference to the electromagnetically oscillatable unit a comparatively high dielectric loss factor and a comparatively small transmittance. If, further, the density of the medium and/or the temperature of the medium are taken into consideration, the salt content a medium, for example, a food, can be ascertained from the deviation of the dielectric constant ascertained for a certain medium from the value 5.9

Many different options are available for the particular geometric embodiment of an apparatus of the invention, of which two especially preferred variants will now be described. The wide range of possible embodiments relates, in such case, both to the arrangement of the at least two sensor elements, thus the at least one mechanically oscillatable unit and the at least one electromagnetically oscillatable unit, as well as also to the embodiment of the at least one electronics unit, which, among other things, includes the control unit associated with the mechanically oscillatable unit, as well as also the coupling unit associated with the electromagnetically oscillatable unit, as well as the active element. Furthermore, the at least one electronics unit can also have the at least one evaluation unit, by means of which the at least one process variable is determined, for example, based on an evaluation algorithm furnished and running in a microprocessor.

In an especially preferred embodiment, the electromagnetically oscillatable unit is arranged on at least one portion or within at least one portion of the mechanically oscillatable unit, or together with, within, or as part of the driving/receiving unit. This is, in such case, a space saving embodiment, where it is assured that the electromagnetically oscillatable unit is arranged in the immediate vicinity of the medium. The utilized materials must, in this case, be matched to the particular geometric arrangement in such a manner that electromagnetic waves propagating within the electromagnetically oscillatable unit can propagate at least partially in the medium. The mechanically oscillatable unit and/or at least one part of the driving/receiving unit should thus especially have a high transmittance for the electromagnetic waves. Especially advantageous for such an embodiment of the present invention is, in given cases, the application of a synthetic material at least for a part of the mechanically oscillatable unit and/or the at least one housing the driving/receiving unit.

In an embodiment, at least one mechanically oscillatable unit in the form of an oscillatory fork having first and second fork tines and at least one electromagnetically oscillatable unit is provided with at least a first conductive trace and a second conductive trace.

For this embodiment, advantageously, the first conductive trace of at least one of the at least one electromagnetically oscillatable unit is at least partially arranged in the interior of the first fork tine and the second conductive trace of such electromagnetically oscillatable unit is at least partially arranged in the interior of the second fork tine of one of the at least one mechanical oscillatable unit. Alternatively, the first and second conductive traces of at least one of the at least one electromagnetically oscillatable unit can be arranged at least partially in the interior of the same fork tine of the at least one mechanical oscillatable unit. Likewise advantageously, the first and/or second conductive trace of the at least one electromagnetically oscillatable unit are/is arranged within a housing of the driving/receiving unit.

Of course, besides the mentioned variants, yet other embodiments are possible, which likewise fall within the scope of the present invention. For example, the at least first and second conductive traces of the electromagnetically oscillatable unit can have different geometries, especially with reference to their width and/or length. The conductive traces are manufactured preferably of copper; however, of course, also other materials can be used. Furthermore, an option is to arrange a number of electromagnetically oscillatable units within a mechanically oscillatable unit and/or within the driving/receiving unit. By different positioning and orientation relatively to one another, the application spectrum in reference to the ascertainable process variables can be yet further expand; compare also the variants described in German patent, DE102013112025A1.

An especially preferred embodiment provides that at least two electromagnetically oscillatable units are provided, wherein the at least two electromagnetically oscillatable units are arranged and the evaluation unit is embodied in such a manner to ascertain, from a comparison of at least a first output signal of the first electromagnetically oscillatable unit and a second output signal of the second electromagnetically oscillatable unit, the presence of an accretion on the at least one mechanically oscillatable unit. For example, the mechanically oscillatable unit is an oscillatory fork and an accretion formation between the two fork tines should be recognized. Then a first electromagnetically oscillatable unit can be arranged in such a manner that it comes in contact with the medium in the region between the two fork tines, while the second electromagnetically oscillatable unit is arranged in such a manner that it comes in contact with the medium in a region outside of the intermediate space between the two fork tines. In the case of accretion formation between the two fork tines, the output signals ascertained by means of the two electromagnetically oscillatable units begin to differ. Then, for example, a limit value for the deviation of the two output signals from one another can be established and upon the exceeding of this limit value a report and/or warning is generated, that accretion has formed. The detection of accretion between the fork tines of a mechanically oscillatable unit in the form of an oscillatory fork is not directly possible by means of a conventional vibronic measuring device. The approach here for accretion detection can, furthermore, be easily transferred to other embodiments of the mechanically oscillatable unit.

In an additional embodiment, at least one electromagnetically oscillatable unit is arranged in a housing of the driving/receiving unit, wherein the evaluation unit is embodied to ascertain from the output signal of the electromagnetically oscillatable unit the penetration of medium into the housing of the driving/receiving unit. Also in this case, penetration of medium brings about a change in the output signal of the particular electromagnetically oscillatable unit. For example, the penetration of medium into the housing of the driving/receiving unit can be detected based on a marked, especially abrupt, increase of the dielectric constant. Again, then, for example, with the exceeding of a predeterminable limit value for the change of the output signal, a report and/or warning can be generated.

Furthermore, advantageously, supplementally, a temperature sensor for registering the temperature of the medium is present. Such can be, for example, a resistance element, especially a platinum element, especially for example, a so-called PT100 or PT1000 element, an NTC thermistor, especially a so-called NTC resistor, e.g. an NTC thermistor (NTC=Negative Temperature Coefficient), a PTC thermistor, especially a so-called PTC resistor, e.g. a PTC thermistor (PTC=Positive Temperature coefficient) or a so-called IC temperature sensor. The registering of temperature as another process variable yields many metrological advantages, on the one hand, with reference to the number of ascertainable process variables, however, also with reference to the accuracy of measurement. Both individual process variables, such as, for example, in the case of aqueous media their dielectric constants, as well as also electronic components of the apparatus arranged near to the process, especially with reference to their embodiment, can have a temperature dependence.

Besides the varied options for embodiment of the at least two sensor elements, also many different variants are possible with reference to the electronic components of the apparatus of the invention.

A conventional electronics unit of a vibronic sensor includes usually at least one control unit and one evaluation unit. The driving/receiving unit is, as a rule, arranged in the immediate vicinity of the mechanically oscillatable unit interacting therewith. At the same time, the driving/receiving unit is, however, in many cases, part of a fed back electrical oscillatory circuit, by means of which the exciting of the mechanically oscillatable unit to execute mechanical oscillations occurs. By means of the evaluation unit, the received signal received from the mechanically oscillatable unit is evaluated relative to its frequency, phase and/or amplitude, and, based on at least one of these variables, the particular process variable is determined.

In contrast, a conventional electronics unit for a microwave sensor includes at least one active element, a coupling unit and an evaluation unit. The active element is either directly connected with the electromagnetically oscillatable unit, or indirectly via a suitable connection, especially via a plugged connection, for example, for connecting two equally- or differently embodied waveguides. The active element must, however, not be arranged in the immediate vicinity of the respective medium. The active element can, thus, for example, be accommodated in a separate housing containing the remaining components, especially electronic components, of the measuring device. The active element is, furthermore, connected with the coupling unit, which leads the out coupled output signal to an evaluation unit, which evaluates the output signal at least with reference to its frequency and based on the frequency evaluation determines the particular process variable. The microwave sensor can be operated in two operating modes, in a continuous mode or in a pulsed mode, wherein the pulsed mode is clearly more energy saving. Variants for the embodiment of a suitable evaluation unit are described, for example, in the Offenlegungsschriften (laid open German applications), DE102012104075A1 and DE102013112025A1.

It is, now, on the one hand, possible to arrange and to contact the electronic components of an apparatus of the invention separately according to oscillatable unit, thus according to sensor element. It is possible, however, also to join a number of components, e.g. arrange them in a shared electronics unit. Also, the electrical contacting of the at least two sensor elements can at least partially be combined.

A possible embodiment provides that at least two electronic units and one evaluation unit are provided, wherein the first electronics unit includes at least the control unit, wherein the second electronics unit includes at least the active element and the coupling unit, and wherein the evaluation unit is embodied, from the received signal and/or the output signal, to determine at least one process variable. Each of the two electronic units is, in this case, electrically connected with the superordinated evaluation unit.

Alternatively, according to another possible embodiment, at least two electronic units are provided, wherein the first electronics unit includes at least the control unit and a first evaluation unit, which can ascertain at least from the received signal at least one process variable, and wherein the second electronics unit includes at least the active element, the coupling unit and a second evaluation unit, which can ascertain at least from the output signal at least one process variable. The at least two evaluating units can, however, also be arranged separately from the residual electronic components of the at least two electronic units. The at least two electronic units can, furthermore, be embodied to communicate with one another. Especially, the master/slave principle can be used at least for data transmission to a superordinated process control system and/or the supplying of the sensor elements, in the case, in which the process variables determined by means of both evaluating units are transmitted via the same lines.

In order to avoid a mutual influencing of measurement operation with reference to the mechanically oscillatable unit and the electromagnetically oscillatable unit, in a preferred embodiment, the electromagnetically oscillatable unit oscillates with a frequency in the range from 100 MHz to 100 GHz and the mechanically oscillatable unit with a frequency in the range from 100 Hz to 100 kHz.

In the case, in which the contacting of the two sensor elements with their electronic components occurs at least partially via the same line or the same lines, it is advantageous, when a trigger unit is provided, which trigger unit is embodied to trigger at least the out-coupling of the output signal on a certain time interval ascertainable based on the exciting signal as a function of time, especially at a time interval having a zero crossing or an extreme-value of the exciter signal. In this case, the electromagnetically oscillatable unit is operated in a pulsed mode.

BRIEF DESCRIPTION OF THE DRAWINGS

The invention as well as its advantageous embodiments will now be described in greater detail based on the appended drawing, the figures of which show as follows:

FIG. 5(a-b) show two possible variants of the electronic components of an apparatus of the invention.

DETAILED DISCUSSION IN CONJUNCTION WITH THE DRAWINGS

Figure 1:
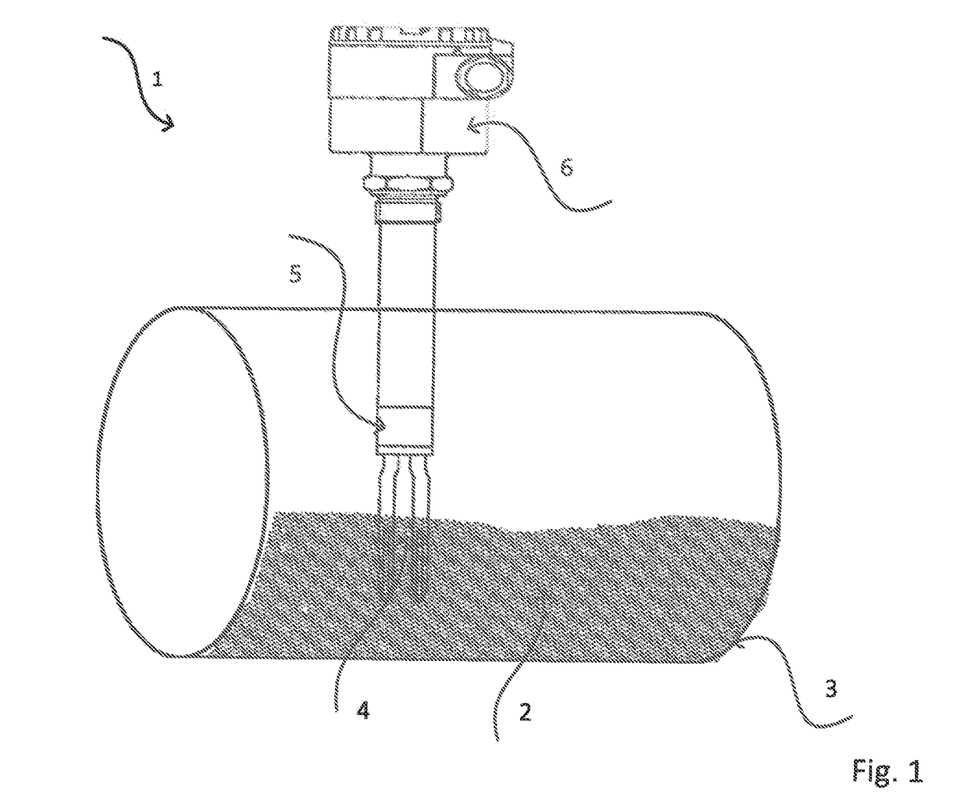
FIG. 1 is a schematic view of a vibronic sensor according to state of the art.

FIG. 1 shows an apparatus 1 in the form of a vibronic sensor 1 for determining and/or monitoring at least one process variable. Shown is a mechanically oscillatable unit 4 in the form of an oscillatory fork, which is partially immersed in a medium 2 located in a container 3. The following description focuses on mechanically oscillatable units 4 in the form of an oscillatory fork. However, there is no intention to limit the general applicability of the invention. Especially for embodiments, in which at least one electromagnetically oscillatable unit 7 is arranged at least partially within the mechanically oscillatable unit 4, it is advantageous to manufacture at least the two fork tines of the mechanically oscillatable unit 4 of a synthetic material in the form of a plastic.

The oscillatable unit 4 is excited by means of the driving/receiving unit 5 to execute mechanical oscillations. Driving/receiving unit 5 can be, for example, a piezoelectric stack- or bimorph drive. However, also other embodiments of a vibronic sensor fall within the scope of the invention. Also shown is an electronics unit 6, by means of which signal registration,—evaluation and/or—feeding occurs.

An apparatus of the invention includes besides a mechanically oscillatable unit 4 also an electromagnetically oscillatable unit 7. Regarding the arrangement of the mechanically oscillatable unit 4 and the electromagnetically oscillatable unit 7, various options are available. An especially space saving embodiment results when the at least one electromagnetically oscillatable unit 7 is arranged at least partially on or in at least one in portion of the mechanically oscillatable unit 4. The following description focuses on these kinds of embodiments. It is not intended, however, to limit the general applicability of the invention. For the case of a mechanically oscillatable unit 4 in the form of an oscillatory fork with two fork tines 4a, 4b and a driving/receiving unit 5 directly adjoining these and an electromagnetically oscillatable unit 7 with at least two conductive traces 7a, 7b, FIG. 2 shows, by way of example, three different forms of embodiment. The illustrated concepts can also be easily transferred to other embodiments of the at least one mechanically oscillatable unit 4 and the at least one electromagnetically oscillatable unit 7.

Figure 2A:
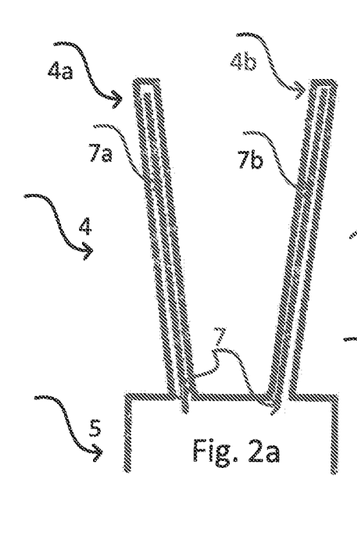
FIG. 2 shows three schematic views of an apparatus of the invention with an oscillatory fork as mechanically oscillatable unit and an electromagnetically oscillatable unit comprising at least two conductive traces, wherein, in (a) each fork tine contains a conductive trace, in (b) two conductive traces are arranged in the same fork tine and in (c) the at least two conductive traces are arranged within the electromagnetically oscillatable unit.

In the embodiment of FIG. 2a, the first conductive trace 7a of the electromagnetically oscillatable unit 7 is arranged in the first fork tine 4a of the mechanically oscillatable unit 4, while the second conductive trace 7b is located in the second fork tine 4b. In this example, of concern is a symmetric arrangement of two equally embodied, conductive traces 7a, 7b, which are insulated completely from the medium by the two fork tines 4a, 4b. In contrast, in the case of the embodiment of FIG. 2b, the two conductive traces 7a, 7b of the electromagnetically oscillatable unit 7 are arranged in the first fork tine 4a of the mechanically oscillatable unit 4, and, in the case of the example of an embodiment according to FIG. 2c, the electromagnetically magneto oscillatable unit 7 is, finally, positioned completely within the housing 5a of the driving/receiving unit 5.

Figure 2B:
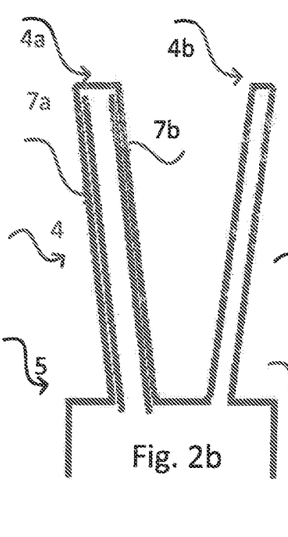
Figure 2C:
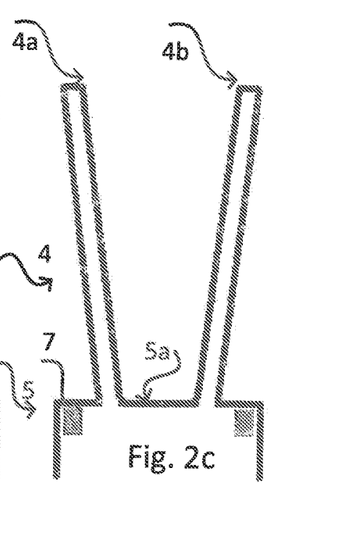
Figure 3A:
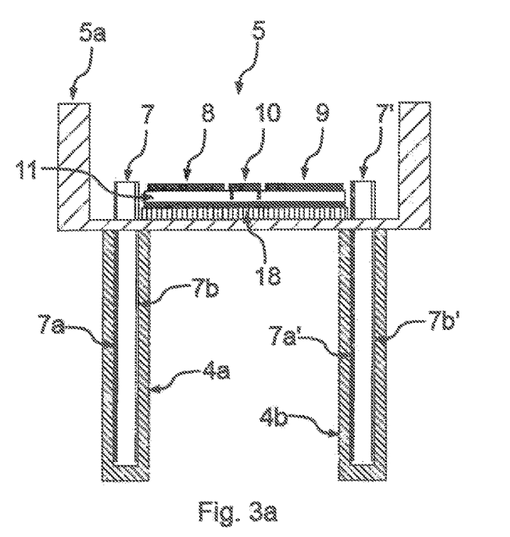
FIG. 3 is an embodiment of an apparatus of the invention with at least two electromagnetically oscillatable units, which are arranged within a mechanically oscillatable unit in the form of an oscillatory fork, wherein (a) is a first side view, (b) a second side view, (c) a detail view of the at least two conductive traces of one of the electromagnetically oscillatable units, and (d) a possible field distribution of the propagating electromagnetic waves emitted from the two electromagnetically oscillatable units.

For all examples shown in FIG. 2, in each case, an electromagnetically oscillatable unit 7 is arranged within a mechanically oscillatable unit 4, respectively within the housing 5a of the associated driving/receiving unit 5. However, also more than one electromagnetically oscillatable unit 7 can be provided. Especially, a number of electromagnetically oscillatable units 7 can be arranged within the same mechanically oscillatable unit 4, such as for the case shown in FIG. 3 of two electromagnetically oscillatable units 7, 7', which are arranged in the two fork tines 4a,4b of a mechanically oscillatable unit 4 in the form of an oscillatory fork. A side view of an example of such an apparatus is shown in FIG. 3a. A first electromagnetically oscillatable unit 7 with two conductive traces 7a, 7b is arranged within the first fork tine 4a of the mechanically oscillatable unit 4, similarly to the example shown in FIG. 2b). However, according to FIG. 3a, a second electromagnetically oscillatable unit 7', likewise with two conductive traces 7a' and 7b', is provided, which is located within the second fork tine 4b. The two electromagnetically oscillatable units 7, 7' are equally embodied and positioned symmetrically to one another within the two fork tines 4a, 4b, in order not to influence the oscillatory behavior of the mechanically oscillatable unit 4. A symmetric arrangement of the at least one electromagnetically oscillatable unit 7 within the mechanically oscillatable unit 4 is therefore generally preferable.

The driving/receiving unit 5 with the housing 5a includes for the example shown in FIG. 3 a so-called piezoelectric bimorph-drive with a disk shaped piezoelectric element 11, on whose one face are arranged in a first region a transmission electrode 8 and in a second region a receiving electrode 9. The transmission electrode 8 and receiving electrode 9 are here embodied equally in form and positioned axially symmetrically to one another. Furthermore, there is located in a third region extending symmetrically around the mirror axis of the transmission electrode 8 and receiving electrode 9 a reference electrode 10, which can lie either at an undefined potential, or, for example, can serve as a ground potential. Beneath the piezoelectric element 11 is, furthermore, a steatite disk 18. In such case, also another material, especially a circuit board material, can be used. Furthermore, also other embodiments of the driving/receiving unit 5 are possible.

Figure 3B:
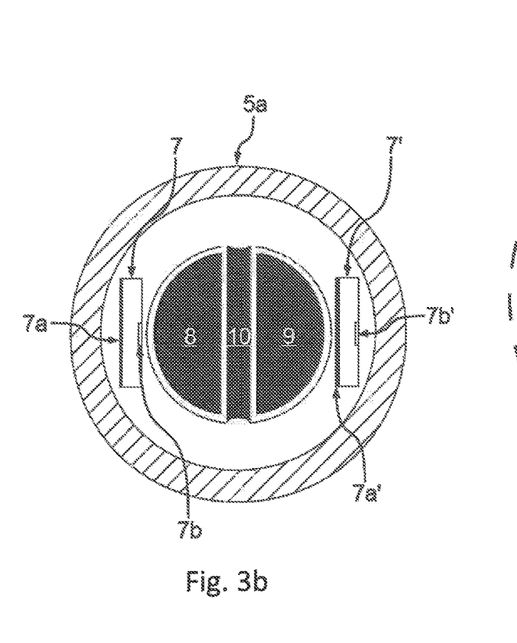

FIG. 3b shows a two dimensional view of the same arrangement turned by 90° from the view of FIG. 3a. From this perspective, it can be seen that for each of the two electromagnetically oscillatable units 7, 7', in each case, the geometry of the first conductive traces 7a, 7a' and the second conductive traces 7b, 7b' differ. These differences are better shown in FIG. 3c in the detail view of the two conductive traces 7a, 7a', 7b, 7b' of the electromagnetically oscillatable units 7, 7'. The first conductive trace 7a, 7a' are narrower with reference to the width of a fork tine 4a, 4b of the mechanically oscillatable unit 4 than the second conductive traces 7b, 7b'. Each of the two electromagnetically oscillatable units 7, 7' can be, thus, be formed from two trace layers, which are insulated from one another, for example, by a plastics layer. For example, a two ply circuit board can be used. In each case, one of the two conductive traces 7a, 7a' or 7b, 7b' is connected with earth or ground. In the example of FIG. 3, this is, in each case, the wider, second conductive trace 7b, 7b'. The electromagnetically oscillatable units 7, 7' are advantageously surrounded by plastic, which besides a protective action also provides a galvanic isolation from the medium 2. Such a galvanic isolation must then no longer be provided within the electronic components 6 of the apparatus 1.

Figure 3C:
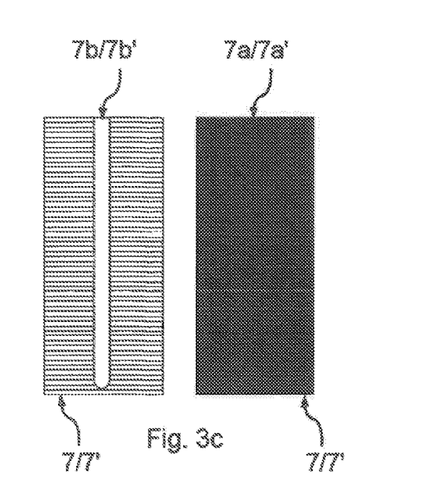
Figure 3D:
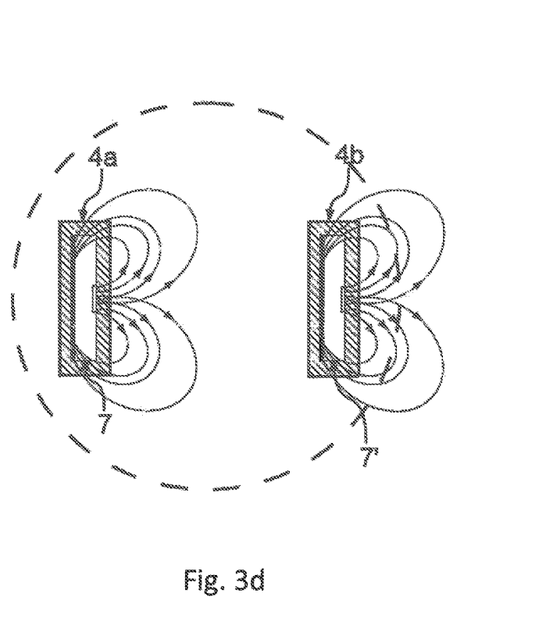

From the embodiment of an apparatus of the invention shown in FIGS. 3a-3c, there results for the electromagnetic field a field distribution such as shown schematically in FIG. 3d. For each of the two electromagnetically oscillatable units 7, 7', a comparatively high field density results in the spatial region adjoining the second conductive trace 7b, 713'. FIG. 3d shows that the first electromagnetically oscillatable unit 7 is, for example, sensitive for the intermediate space between the two fork tines 4a, 4b, while the second electromagnetically oscillatable unit 7' is sensitive for a spatial region outside of the intermediate space between the two fork tines 4a, 4b. Then, the permittivity, permeability, index of refraction or also dielectric loss factor can be determined, for example, advantageously by means of the second electromagnetically oscillatable unit 7'. From a deviation from a comparison value of the particular process variable, as ascertained based on the first electromagnetically oscillatable unit 7, it can, furthermore, be detected that accretion is forming between the two fork tines 4a, 4b. It is to be noted here that the geometry of the electromagnetically oscillatable units 7, 7' can be optimized for a particular application, for example, in such a manner that an as great as possible spatial region or a smaller spatial region is registrable as exactly as possible, e.g by coordinating where the electromagnetic field reaches. Of course, instead of making the two electromagnetically oscillatable units 7, 7' parallel, in the case of which the first broadly executed conductive traces 7a, 7a' are arranged left and the second more narrowly executed conductive traces 7b, 7b' are arranged right, for example, also an antiparallel arrangement of the two electromagnetically oscillatable units 7, 7' is possible, so that the two electromagnetically oscillatable units are sensitive for a spatial region outside of the intermediate space between the two fork tines 4a, 4b. In this case, for example, besides the actual process variable determination, differential accretion on the external sides of the fork tine 4a, 4b can be detected. The knowledge concerning accretion formation can, in such case, affect the accuracy of measurement of the measuring device advantageously.

Another possible embodiment of the present invention is, finally, subject matter of FIG. 4. The driving/receiving unit 5 comprises, such as in the embodiment of FIG. 3, a piezoelectric bimorph drive. As evident from FIG. 4a, an electromagnetically oscillatable unit 7 is arranged within the housing 5a of the driving/receiving unit 5 in the form of two essentially annular, conductive traces 7a, 7b, which are located on two oppositely lying faces of the steatite disk 18. The exact arrangement of the electromagnetically oscillatable unit 7 can, however, be more exactly detected based on the detailed views in FIG. 4b and FIG. 4c. In the example shown in FIG. 4b, the second trace 7b is embodied ring-shaped and arranged in the region of a first, in this example, circularly round face of the steatite disk 18. Instead of the steatite disk 18, for example, also a circuit board can be used. The second conductive trace 7b is, furthermore, contacted via an electrically conductive contact extending from the first to the second face of the steatite disk 18 lying opposite to the first face. Arranged on this second face is, moreover, the first conductive trace 7a in the form of an open (i.e. not closed) ring section of opening length u. The first conductive trace extends partially, i.e. not completely, around the piezoelectric element 11 bearing the electrodes 8,9 and 10. The length of the opening u can, in such case, be selected suitably as a function of the application. It is to be noted here that this example of an embodiment basically can be modified in many different ways. For example, the second conductive trace can also be provided in the form of a complete circle or in the form of a circular section, however, also in the form of a two-dimensional geometric area of other geometry. Also, the conductive traces 7a,7b can be arranged differently within the housing of the driving/receiving unit, i.e. differently embodied electromagnetically oscillatable units 7 can be applied.

Figure 4A:
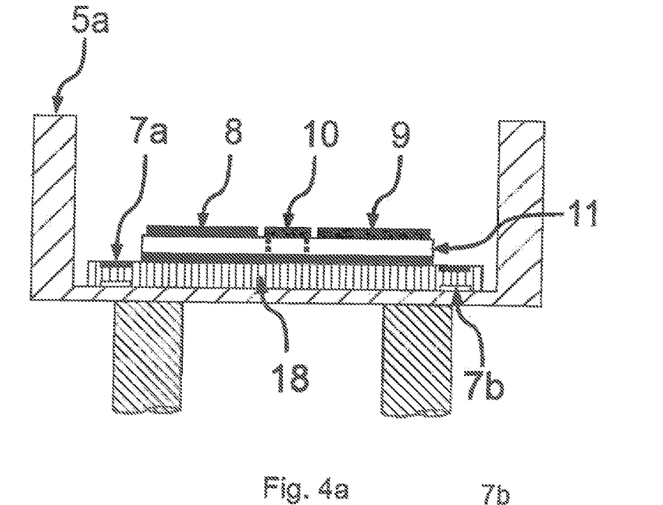
FIG. 4 is an embodiment of an apparatus of the invention according to FIG. 2c), wherein (a) is a side view, (b) and (c) are detailed views of the driving/receiving unit as well as the two conductive traces of the electromagnetically oscillatable unit and (d) a possible field distribution of the propagating electromagnetic waves emitted from the electromagnetically oscillatable units.
Figure 4B:
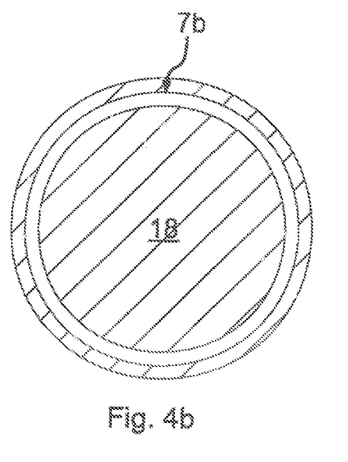
Figure 4C:
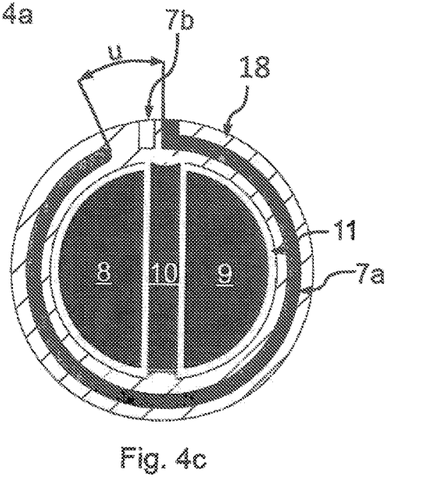
Figure 4D:
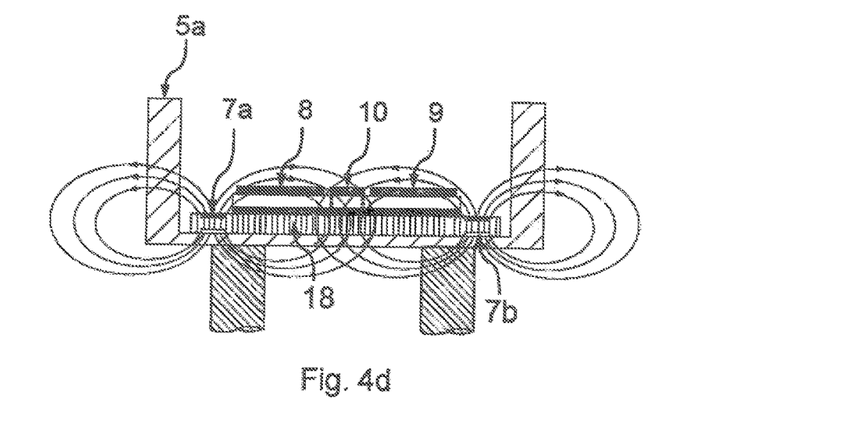

The small separation of the two conductive traces 7a,7b in this example permits choice of a comparatively high frequency, whereby the particular electromagnetic field propagates only in a comparatively small spatial region and results in a high sensitivity of the arrangement. The resulting field distribution is indicated in FIG. 4d. Depending on geometrical design of the electromagnetically oscillatable unit 7, such an arrangement can also be used for detecting the penetration of medium into the housing 5a of the driving/receiving unit.

Figure 5A:
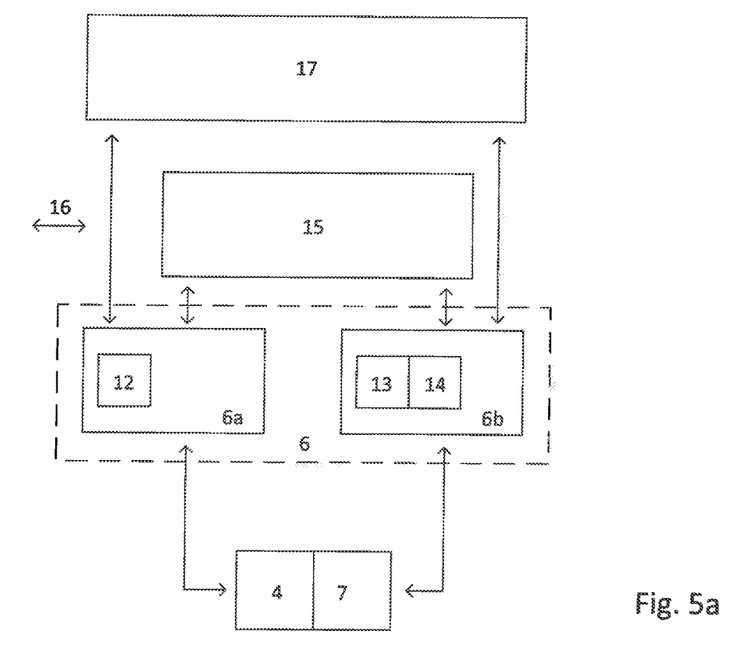
Figure 5B:
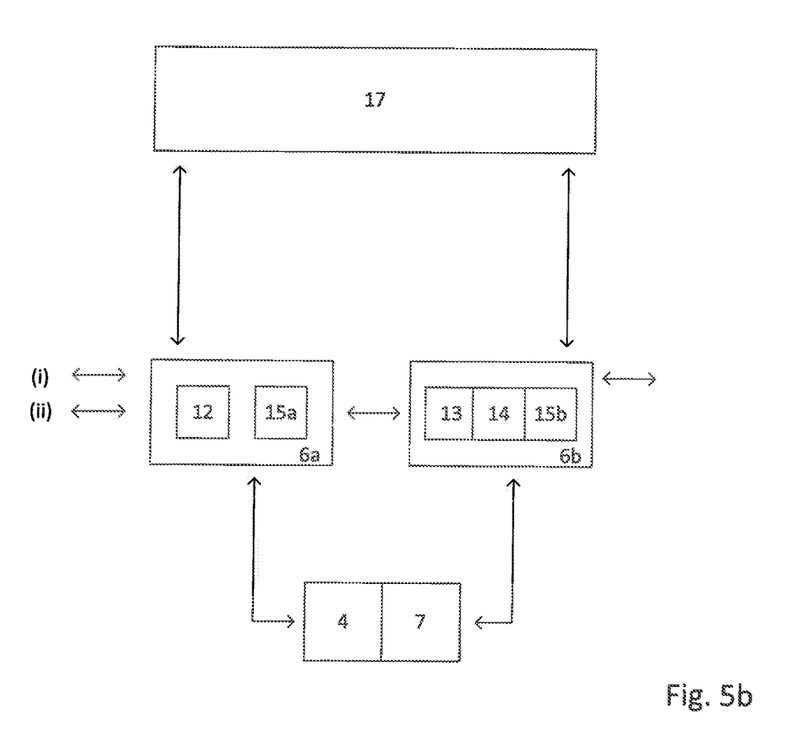

Finally, FIG. 5a and FIG. 5b show, in the form two block diagrams, two possible embodiments for the electronic components of an apparatus of the invention. In the example according to FIG. 5a, a first 6a and a second electronics unit 6b are provided. The first electronics unit 6a is connected with the mechanically oscillatable unit 4 by means of the driving/receiving unit (here not separately shown) and includes at least the control unit 12, which at least is embodied to produce the exciter signal starting from the received signal, and to set a predeterminable phase shift between the exciter signal and the received signal. The second electronics unit 6b is, in turn, connected with the electromagnetically oscillatable unit 7 and includes at least the active element 13 and the coupling unit 14. The two electronic units 6a, 6b are, in turn, connected with an evaluation unit 15, within which at least the at least one process variable is determined. In such case, the evaluation unit 15 includes, for example, a microprocessor. Moreover, it can also have a memory unit.

The evaluation unit 15 can, furthermore, be connected with a superordinated control system 16.

Optionally, moreover, a trigger unit 17 can be provided. This is useful especially in the case of a pulsed operation of the electromagnetically oscillatable unit 7. The trigger unit triggers at least the out-coupling of the output signal on a certain time interval ascertainable based on the exciting signal as a function of time, especially upon a time interval having a zero crossing or an extreme-value of the exciter signal. Operation triggered in such a manner is distinguished, on the one hand, by an especially low power consumption. On the other hand, a possible mutual influencing of the output signal and the exciter- and/or received signal is minimized.

Alternatively to the example shown in FIG. 5a, the first and second electronics units can also be put together in a superordinated electronics unit 6 (dashed box). Also, the evaluation unit 15 as well as the trigger unit 17 can be arranged in this electronics unit 6.

A second variant of an arrangement of the invention of the electronic components is shown in FIG. 5b. In this case, two separate evaluating units 15a, 15b are provided, wherein the first evaluation unit 15a is associated with the first electronics unit 6a and is embodied for determining a process variable at least from the received signal of the mechanically oscillatable unit 4, and wherein the second evaluation unit 15b is associated with the second electronics unit 6b and is designed for determining a process variable at least from the output signal of the electromagnetically oscillatable unit 7. The two evaluating units 15a, 15b can, of course, also be arranged separately from the two electronic units 6a, 6b. Again, optionally also a trigger unit 17 can be provided.

There are a number of options in the case of this embodiment for a connection desired, in given cases, with a superordinated control system. For instance, each of the two evaluating units 15a, 15b can be connected with the superordinated control system (case i). Alternatively, the two evaluating units 15a,15b can, however, also be connected with one another (case ii). Then, it is sufficient that just one of the two evaluating units 15a,15b (in the example shown here, the first evaluation unit 15a) is connected with a superordinated control system. The communication between the two evaluating units 15a,15b can then occur, for example, according to the master/slave principle.

The invention claimed is:

1. An apparatus for determining and/or monitoring at least one process variable of a medium in a container, comprising:
   a mechanically oscillatable unit;
   a driving/receiving unit for exciting said mechanically oscillatable unit to execute mechanical oscillations by means of an electrical, exciting signal and for receiving and transducing the mechanical oscillations into an electrical, received signal;
   a control unit, which is embodied to produce the exciter signal starting from the received signal and to set a predeterminable phase shift between the exciter signal and the received signal;
   an electromagnetically oscillatable unit;
   an active element for producing and/or maintaining electromagnetic oscillations in said electromagnetically oscillatable unit, which active element forms together with said electromagnetically oscillatable unit an oscillator;
   a coupling unit, which is embodied to tap an output signal from said active element; and
   an evaluation unit, wherein:
   said evaluation unit is embodied to determine the at least one process variable from the received signal and/or from the output signal; and
   wherein said at least one mechanically oscillatable unit is in the form of an oscillatory fork having a first fork tine and a second fork tine, and said at least one electromagnetically oscillatable unit is provided with at least a first conductive trace and a second conductive trace.

2. The apparatus as claimed in claim 1, wherein:
   said mechanically oscillatable unit is a membrane, a single rod, or an oscillatory fork.

3. The apparatus as claimed in claim 1, wherein:
   said mechanically oscillatable unit is manufactured of a metal, a ceramic or a synthetic material.

4. The apparatus as claimed in claim 1, wherein:
said driving/receiving unit includes at least one piezoelectric element or at least one coil.

5. The apparatus as claimed in claim 1, wherein:
said electromagnetically oscillatable unit is embodied as a waveguide, especially as a coaxial cable, hollow conductor, or microstrip transmission line, as a patch antenna, as a dielectric gradient conductor or as a two-wire line.

6. The apparatus as claimed in claim 1, wherein:
said at least one process variable is a fill level or limit-level of the medium in the container, the viscosity, the density, the permittivity, the permeability, the dielectric loss factor, the protein content and/or fat content of a medium, especially a food, or the water fraction in an oil.

7. The apparatus as claimed in claim 1, wherein:
said electromagnetically oscillatable unit is arranged on at least one portion or within at least one portion of said mechanically oscillatable unit or together with, within, or as part of said driving/receiving unit.

8. The apparatus as claimed in claim 1, wherein:
said first conductive trace of said at least one of the at least one electromagnetically oscillatable unit is at least partially arranged in the interior of said first fork tine and said second conductive trace of said electromagnetically oscillatable unit is at least partially arranged in the interior of said second fork tine of said at least one mechanical oscillatable unit.

9. The apparatus as claimed in claim 1, wherein:
said first and said second conductive trace of at least one of said at least one electromagnetically oscillatable unit is arranged at least partially in the interior of the same fork tine of said at least one mechanical oscillatable unit.

10. The apparatus as claimed in claim 1, wherein:
said first and/or said second conductive trace of said least one electromagnetically oscillatable unit are/is arranged within a housing of said driving/receiving unit.

11. The apparatus as claimed in claim 1, wherein:
at least two electromagnetically oscillatable units are provided; and
said at least two electromagnetically oscillatable units are arranged and said at least one evaluation unit is embodied in such a manner to ascertain, from a comparison of at least a first output signal of said first electromagnetically oscillatable unit and a second output signal of said second electromagnetically oscillatable unit, presence of an accretion on said at least one mechanically oscillatable unit.

12. The apparatus as claimed in claim 1, wherein:
at least one electromagnetically oscillatable unit is arranged in a housing of said driving/receiving unit; and
said evaluation unit is embodied to ascertain, from the output signal of said electromagnetically oscillatable unit, penetration of medium into said housing of said driving/receiving unit.

13. The apparatus as claimed in claim 1, further comprising:
a temperature sensor for registering temperature of the medium is present.

14. The apparatus as claimed in claim 1, wherein:
said electromagnetically oscillatable unit oscillates with a frequency in the range from 100 MHz to 100 GHz; and/or
said mechanically oscillatable unit oscillates with a frequency in the range from 100 Hz to 100 kHz.

15. The apparatus as claimed claim 1, wherein:
a trigger unit is provided, which trigger unit is embodied to trigger at least the out-coupling of the output signal on a certain time interval ascertainable based on the exciting signal as a function of time, especially at a time interval having a zero crossing or an extreme-value of the exciter signal.

* * * * *